United States Patent [19]
Barrows et al.

[11] Patent Number: 5,286,837
[45] Date of Patent: Feb. 15, 1994

[54] PROCESS FOR INCREASING STABILITY OF POLY(ESTERAMIDES)

[75] Inventors: Thomas H. Barrows, Cottage Grove; Myhanh T. Truong, Blaine; Paul R. Suszko, Cottage Grove; David W. Stegink, Mendota Heights, all of Minn.

[73] Assignee: Minnesota Mining and Manufacturing Company, St. Paul, Minn.

[21] Appl. No.: 986,665

[22] Filed: Dec. 8, 1992

Related U.S. Application Data

[63] Continuation-in-part of Ser. No. 821,406, Jan. 15, 1992, abandoned.

[51] Int. Cl.$^5$ .................. C08G 73/10; C08G 63/68
[52] U.S. Cl. .................. 528/291; 528/281; 528/285; 528/335; 528/336; 528/341; 528/361; 528/367; 528/370; 528/492
[58] Field of Search ............... 528/291, 492, 361, 367, 528/370, 281, 285, 335, 336, 341

[56] References Cited

U.S. PATENT DOCUMENTS

| | | | |
|---|---|---|---|
| 4,209,607 | 6/1980 | Shalaby et al. | 528/291 |
| 4,226,243 | 10/1980 | Shalaby et al. | 128/335.5 |
| 4,343,931 | 8/1982 | Barrows | 528/291 |
| 4,529,792 | 7/1985 | Barrows | 528/291 |
| 4,534,349 | 8/1985 | Barrows | 128/334 R |
| 4,669,474 | 6/1987 | Barrows | 128/334 C |
| 4,672,094 | 6/1987 | Nelb, II et al. | 525/440 |
| 4,719,917 | 1/1988 | Barrows et al. | 128/334 R |
| 4,883,618 | 11/1989 | Barrows | 264/49 |
| 5,013,315 | 5/1991 | Barrows | 606/71 |

FOREIGN PATENT DOCUMENTS 3086678.6 12/1984 European Pat. Off. .
14840 7/1981 France .

OTHER PUBLICATIONS

T. H. Barrows, "Degradable implant materials: a review of synthetic absorbable polymers ad their applications", *Clinical Materials*, 1986; 1:233–257.

Vicki L. Horton, Paula E. Blegen, Thomas H. Barrows, Gregory J. Quarfoth, Sheila J. Gibson, James D. Johnson, and Roy L. McQuinn, "Comparison of Bioabsorbable Poly(Ester-Amide) Monomers and Polymers in Vivo Using Radiolabeled Homologs", *Progress in Biomedical Polymers*, C. G. Gebelein and R. L. Dunn, Eds., Plenum Press, New York, 1990, pp. 263–282.

T. H. Barrows, J. D. Johnson, S. J. Gibson, and D. M. Grussing, "The Design and Synthesis of Bioabsorbable Poly(Ester-Amides)".

S. Andini et al., "Synthesis of block polyesteramides containing biodegradable poly(L,L-lactide) segments", *Makromolekulare Chemie, Rapid Communications*, vol. 9, No. 3, Mar. 1988, pp. 119–124.

Database WPI, Derwent Publications Ltd., London, GB; AN 192653 and JP A60118714, Jun. 26, 1985.

*Primary Examiner*—John Kight
*Assistant Examiner*—Shelley A. Dodson
*Attorney, Agent, or Firm*—Gary L. Griswold; Walter N. Kirn; Robert H. Jordan

[57] ABSTRACT

Process for treating poly(esteramides) to improve the heat and storage stability thereof. Polymer is optionally suspended in a liquid medium, treated with an amide group-containing solvent, and then separated from the solvent and liquid medium (if any). Also, poly(esteramides) treated in this process and devices and articles comprising such poly(esteramides).

39 Claims, No Drawings

PROCESS FOR INCREASING STABILITY OF POLY(ESTERAMIDES)

CROSS-REFERENCE TO RELATED APPLICATION

This application is a continuation-in-part of application Ser. No. 07/821,406, filed Jan. 15, 1992, now abandoned.

FIELD OF INVENTION

The present invention relates to a process for treating poly(esteramides) to increase the heat and storage stability thereof.

BACKGROUND OF THE INVENTION

Poly(esteramides) are known to be useful bioabsorbable polymeric materials derived from reacting diamidediols with dicarboxylic acids, derivatives thereof or bischloroformates. Such polymers and some of their uses are described in U.S. Pat. Nos. 4,343,931; 4,529,792; 4,534,349; 4,669,474; 4,719,917; 4,883,618; and 5,013,315 (all Barrows et al.).

An increasing number of surgically implantable devices that only function for a relatively short period of time in vivo are being designed from synthetic polymers that are eliminated from the body by hydrolytic degradation and subsequent metabolism after serving their intended purpose. The molecular weight of such "bioabsorbable" polymers is an important parameter in determining whether or not a particular lot of polymer will perform properly for an adequate length of time in any specific application. Thus, if significant loss of molecular weight occurs during processing of the polymer to fabricate a device, such as by melt extrusion, then the device may fail prematurely in vivo as hydrolysis shifts the molecular weight distribution below a minimum range required for the device to function properly. Some causes which may lead to reduction in molecular weight and premature device failure include degradation due to melt processing conditions (e.g., the high temperature and shear conditions encountered during extrusion processing), due to moisture in the polymer, and due to synthesis residues (e.g., unreacted precursor materials and reaction by-products) in the polymer, e.g., acid chlorides.

Loss of molecular weight upon extrusion is commonly encountered with polyesters even when moisture in the resin has been reduced to the lowest possible level. For example, poly-L-lactide, a well known bioabsorbable polyester has not yet been melt extruded into fiber with molecular weight much higher than 100,000 since the extrusion process typically degrades higher molecular weight fractions to this relatively constant maximum value.

Bioabsorbable poly(esteramides) described in U.S. Pat. Nos. 4,343,931 and 4,529,792 offer an advantage over poly-L-lactide and related polyesters in that a lower molecular weight is adequate to achieve comparable fiber strength due to the intermolecular hydrogen bonding provided by the amide linkages. Fibers made of such polymers exhibit comparable strength to those made of poly-L-lactide while providing lower modulus (and thus greater flexibility) and greater toughness and durability. Compared to poly-L-lactide such fibers are also more rapidly bioabsorbed. A disadvantage with poly(esteramides), however, results from the unreliable method of synthesis in which intermediate molecular weight material must be heated as a solid to advance the molecular weight to an acceptable value. If continued too long, this treatment yields excessively crosslinked or "gelled" material which is unsuitable for extrusion. On the other hand, if the process is not continued long enough, the polymer lacks storage and thermal stability due to the presence of unreacted acid chloride functionality.

SUMMARY OF INVENTION

The present invention provides a process for treating body absorbable poly(esteramides) (referred to herein as "PEA") to improve the heat and storage stability thereof. Previously available poly(esteramides) did not provide the excellent heat and storage stability provided by poly(esteramides) treated in accordance with the present invention.

In brief summary, the preferred process of the invention comprises:
a) providing a poly(esteramide) polymer as defined below;
b) suspending the polymer in a non-reactive liquid medium, e.g., an aprotic liquid such as toluene;
c) treating the suspended polymer with an amide group-containing solvent;
d) separating the polymer from the solvent, e.g., precipitating by cooling;
e) removing the solvent; and, typically,
f) removing the liquid medium and drying the polymer to yield the stabilized polymer in powder form.

In some instances, a poly(esteramide) in solid form may be stabilized by:
a) providing a poly(esteramide) polymer as defined below;
b) treating the polymer (e.g., extracting or dissolving) with an amide group-containing solvent; and
c) separating the polymer from the solvent;

thus omitting the suspension of the polymer in the liquid medium. Suspension with a liquid medium as described above is preferred, however, because lesser amounts of solvent may be used (and as noted below the solvent can be a source of moisture) and because PEA will precipitate at a higher temperature from a mixture of solvent and medium than from solvent above, thereby facilitating removal of polymerization of by-products such as HCl which have a higher affinity for the solvent at higher temperature.

Poly(esteramides) treated in accordance with the invention are suitable for use in a variety of devices, for example sutures and other fiber containing devices. In particular, polymers treated in accordance with the invention may be used to advantageous result in devices whose construction entails rigorous conditions, e.g., melt processing such as extrusion.

DETAILED DESCRIPTION OF ILLUSTRATIVE EMBODIMENTS

In general, poly(esteramide) polymers treated by the process of the present invention have the general formula:

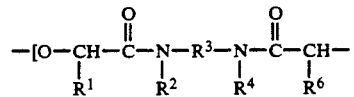

-continued

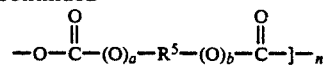

wherein:

a) $R^1$ and $R^6$ are identical or different and are hydrogen or methyl;

b) $R^3$ and $R^5$ are identical or different and are selected from the group consisting of the following, which are linear or branched, alkylene, alkylene having 1 or 2 nonadjacent catenary oxygen or sulfur atoms, alkenylene, cycloalkylene and arylene; the members of the group having up to 25 carbon atoms in the cyclic compounds and from 2 to 25 carbon atoms in the non-cyclic compounds;

c) $R^2$ and $R^4$ are identical or different and are hydrogen or alkyl having 1 to 4 carbon atoms or $R^2$ and $R^4$ together are linear or branched alkylene having one to four carbons forming with N—$R^3$—N a heterocyclic group having 5 or 6 ring atoms;

d) a and b are independently zero or one; and e) n having an average value from about 10 to about 400.

To manufacture fibers which have nylon-like flexibility and strength properties, $R^2$ and $R^4$ are preferably both hydrogen so as to facilitate hydrogen bonding.

We have observed that when at least one of $R^3$ and $R^5$ is relatively short (i.e., about 2 to 4 carbon atoms), fibers made from the resultant polymer offer superior results; whereas if both $R^3$ and $R^5$ are relatively long (i.e., about 6 to 14 carbon atoms), the resultant fibers do not provide comparable results. Polymers of the invention where $R^3$ is linear alkylene of 2 to 14 carbon atoms are presently preferred. Polymers of the invention where $R^5$ is linear alkylene of 2 to 14 carbon atoms are presently preferred, and most preferred is alkylene of 4 to 12 carbon atoms.

Polymers of the invention wherein a and b are zero are presently preferred because it is easier to manufacture polymers with higher molecular weight.

Polymers of the invention wherein n is 10 to 400 are presently preferred because such polymers provide a more generally useful combination of strength and rate of in vivo absorption. Most preferred are polymers wherein n is about 50 to 200 because such polymers provide what is generally an optimal balance of strength and rate of in vivo absorption. Polymers with relatively lower molecular weight (i.e., relatively smaller n) provide lower strength with faster absorption whereas polymers with relatively higher molecular weight (i.e., relatively larger n) provide greater strength and with slower absorption.

It has been found that polymers (and fibers formed therefrom) based on diamidediols formed from 1,2-ethanediamine and glycolic or lactic acids manifest particularly significant improvements in properties when treated in accordance with the process of the invention. Unless treated in accordance with the invention, such polymers have been observed to be more subject to breakdown during melt processing than some other poly(esteramides).

As mentioned above, in brief summary, the process of the invention comprises:

a) providing a PEA as described above;

b) preferably suspending the polymer in a non-reactive liquid medium;

c) treating, preferably dissolving, the preferably suspended polymer with an amide group-containing solvent;

d) separating the polymer, e.g., precipitating it;

e) removing the solvent; and, typically, f) removing the liquid medium if any and drying the polymer to yield the stabilized polymer in powder form.

The treatment may be applied to PEA which is initially in dry form, or may be incorporated as part of the initial PEA synthesis process.

When synthesizing PEA, in order to obtain the regular sequence shown in the formula above, it is typically desirable to first form the amide linkages prior to PEA-forming or stage 2 polymerization. This can be accomplished by combining about two moles of glycolic or lactic acid, or a combination thereof, with about one mole of diamine and heating at a temperature between about 150° and about 220° C. until distillation of water is complete. Alternatively, combination of hydroxy acid and diamine will produce a salt which can be purified by recrystallization and then subjected to the above condensation. In either case, a high yield of diamidediol is obtained which should be purified by recrystallization.

Synthesis of preferred PEA polymers with an inherent viscosity suitable to obtain fibers with adequate strength is preferably carried out as described herein. The preferred process for forming poly(esteramides) having a suitably high molecular weight (i.e., n is 10 or more) comprises:

a) suspending one or more diamidediols, preferably in powder form, in an aprotic liquid (referred to herein as a "synthesis solvent") which: 1) is a nonreactive solvent for acid chlorides, 2) is nonsolvent for diamidediols, 3) has a boiling point of 100° C. or higher, and 4) is preferably substantially free of water;

b) adding a stoichiometrically equal amount of one or more diacid chlorides;

c) heating the mixture to a moderate temperature, e.g., about 60° to about 90° C., until low molecular weight, i.e., an inherent viscosity between about 0.3 and about 0.6, is achieved; and then d) rapidly refluxing with vigorous mechanical mixing (e.g., motor driven paddle), preferably until the polymer has an inherent viscosity of about 1.0 to about 1.2; yielding PEA of the desired formula. By "nonsolvent" it is meant that the subject liquid, at its boiling point, will not solvate more than 2 weight percent of the subject material. Preferably, the liquid will solvate substantially none of the subject material. By "nonreactive" it is meant that the subject liquid will not react with any of the species (precursors, intermediates, and reaction products) of the subject reaction.

The resultant PEA, still suspended in the synthesis solvent, may then be immediately treated in accordance with the process of the invention as described below or it may be reduced to powder form. It is typically preferred to treat the PEA within a week of its synthesis, more preferably immediately after its synthesis, to avoid degradation during storage. If necessary to delay treatment for a time after synthesis, removal of the synthesis solvent is generally preferred to reduce degradation during storage. An advantage of the treatment process of the invention is that typically the PEA can be treated in the same vessel it was synthesized in, typically using the synthesis solvent as the liquid medium.

Preferably the inherent viscosity of the polymer is frequently or continuously monitored throughout the PEA synthesis. As used herein, inherent viscosity is measured at 30° C. in 2,2,2-trifluoroethanol. If the synthesis is halted while the inherent viscosity is still at too low a level, the molecular weight of the resultant polymer will be too low and it will exhibit poor strength and tend to be brittle; whereas if the synthesis is not halted soon enough and the inherent viscosity reaches too high a level, the resultant polymer may gel, at least in some portions. Gelled portions typically lead to weak points in fibers made from such polymers.

Illustrative examples of suitable synthesis solvents, which exhibit desirable nonreactivity and sufficiently high boiling points, include methyl chloroacetate, high boiling ketones, toluene, chlorobenzene, xylene, 1,1,2-trichloroethane, and 1,4-dioxane. The preferred synthesis solvents for use with a diacid chloride are chlorobenzene and toluene because of their useful boiling points. Toluene is most preferred because of its generally held status as a toxicologically safe agent. If desired, mixtures of synthesis solvents may be used. Typically, solvents and solvent mixtures which have boiling points (at 1 atmosphere) of between about 70° C. and about 150° C., preferably between about 90° C. and about 120° C., are useful.

The preferred synthesis process has the advantages of not requiring catalyst, of yielding product in a relatively short period of time, and of producing high molecular weight polymer, typically free of crosslinking, in an easy-to-manipulate form. In addition, moisture which would otherwise react with the acid chloride can be readily excluded from the system by azeotropic distillation prior to addition of the diacid chloride.

Dicarboxylic acid chlorides and the dimethyl or diethyl esters of dicarboxylic acids useful in the synthesis of polymers by the above methods include those derived from dicarboxylic acids listed below. In addition, the free acids can also be used. The term "dicarboxylic acid" as used herein includes dicarboxylic acids, their methyl and ethyl esters, their acid chlorides and anhydrides. The dicarboxylic acids are, for example, oxalic acid; malonic acid, succinic acid; 2,3-dimethylsuccinic acid; glutaric acid,; 3,3-dimethylglutaric acid; 3-methyladipic acid; adipic acid; pimelic acid; suberic acid; azelaic acid; sebacic acid; 1,9-nonanedicarboxylic acid; 1,10-decanedicarboxylic acid; 1,11-undecanedicarboxylic acid; 1,12-dodecanedicarboxylic acid; 1,13-tridecanedicarboxylic acid; 1,14-tetradecanedicarboxylic acid; 1,15-pentadecanedicarboxylic acid; 1,16-hexadecanedicarboxylic acid; maleic acid; trans-$\beta$-hydromuconic acid; fumaric acid; diglycolic acid; 3,3'-oxydipropionic acid; 4,4'-oxydibutyric acid; 5,5'-oxydivaleric acid; 6,6'-oxydicaproic acid; 8,8'-oxydicaprylic acid; 6-oxaundecanedioic acid; 5-oxaazelaic acid; 5-oxasebacic acid; 5-oxaundecanedioic acid; 5-oxadodecanedioic acid; 5-oxatetradecanedioic acid; 5-oxahexadecanedioic acid; 6-oxadodecanedioic acid; 6-oxatridecanedioic acid; 6-oxapentadecanedioic acid; 6-oxaheptadecanedioic acid; 7-oxapentadecanedioic acid; 10-oxanonadecanedioic acid and other oxa-aliphatic dicarboxylic acids; 1,2-cyclobutanedicarboxylic acid; 1,4-cyclohexanedicarboxylic acid and the like. Linear diacids containing two to twelve —CH2— groups are preferred as they degrade into agents known to be metabolically satisfactory. In the presently most preferred polymer, $R^5$ is preferably decane, e.g., formed by the removal of the chloride from dodecanedioyl chloride. It is highly preferred that the acid chlorides be carefully purified, e.g., by fractional distillation.

Diamidediols useful in synthesizing polymers of this invention can be prepared by the above methods from diamines such as 1,2-ethanediamine; 1,3-propanediamine; 1,3-(2-methylpropane)diamine; 1,3-(2,2-dimethylpropane)diamine; 1,2-(1,2-dimethylethane)diamine; 1,4-butanediamine; 1,5-pentanediamine; 1,6-hexanediamine; 1,7-heptanediamine; 1,8-octanediamine; 1,9-nonanediamine; 1,10-decanediamine; 1,11-undecanediamine; 1,12-dodecanediamine; 1,13-tridecanediamine; 1,14-tetradecanediamine; 1,15-pentadecanediamine; 1,16-hexadecanediamine; 3-oxapentane-1,5-diamine; 4-oxaheptane-1,7-diamine; 5-oxanonane-1,9-diamine; 6-oxaundecane-1,11-diamine; 7-oxatridecane-1,13-diamine; 8-oxapentadecane-1,15-diamine; 9-oxaheptadecane-1,17-diamine; 10-oxanonadecane-1,19-diamine; 11-oxahendecacosane-1,21-diamine; 12-oxatricosane-1,23-diamine; 13-oxapentacosane-1,25-diamine; 4,9-dioxadodecane-1,12-diamine; 3,6-dioxaoctane-1,8-diamine and other analogs of oxa-aliphatic diamines and the corresponding thia-aliphatic diamines; cyclohexane-1,4-diamine; cyclohexane-1,3-diamine; cyclohexane-1,2-diamine; 1,4-bis(aminomethyl)cyclohexane; 1,3-bis(aminomethyl)cyclohexane; 1,4-bis(2-aminoethyl)-cyclohexane; 1,4-bis(3-aminopropyl)cyclohexane; bis(4-aminocyclohexyl)methane; p-phenylenediamine; o-phenylenediamine; m-phenylenediamine; p-xylylene-alpha, alpha-diamine and other aromatic diamines; piperazine; 4,4'-trimethylenedipiperidine; 4,4'-bipiperidine; N,N'-bis(3-aminopropyl)piperazine; 2,5-dimethylpiperazine; 2,6-dimethylpiperazine; 2-methylpiperazine; imidazolidine; 2-methylimidazolidine; and 4,5-dimethylimidazolidine.

In the process of the invention, PEA polymer is suspended preferred in a liquid medium. The liquid medium should be a nonreactive, nonsolvent for the PEA. If desired, the liquid medium may be the synthesis solvent described above. In addition, lower boiling point liquids, e.g., ethyl acetate, not considered suitable for use as synthesis solvents may be used as liquid mediums. PEA in dry form may be suspended in the medium, or the synthesis product, still suspended in the synthesis solvent, may be used. As discussed above, it is preferable to treat the PEA as described herein shortly after synthesis. Improved storage stability of PEA is one of the advantages of this invention.

Preferably, the PEA is treated before the polymer crosslinks to a gel. This can be achieved by monitoring the inherent viscosity of the PEA during the synthesis and stopping the synthesis reaction at an appropriate point. It has been observed that PEA tends to aggregate before gelling, the aggregation being observable during inherent viscosity monitoring. In the event that aggregation or slight gelling has occurred, it is often possible to reverse the aggregation or gelling in the course of heating and dissolving the polymer in the solvent.

The suspended PEA is then treated with, e.g., by extracting with, preferably dissolving in, an amide group-containing solvent. Illustrative examples of amide group-containing solvents suitable for use in the treatment process of the invention include N-methylpyrrolidone, N-methylformamide, N-methylacetamide, N,N-dimethylacetamide, formamide, N,N-dimethylformamide, tetramethylurea and the like. Tetramethylurea and N-methylpyrrolidone are preferred, with N-methylpyrrolidone being most preferred, because these solvents are considered toxicologically safe compounds. Typically, PEA treated in accordance with the invention, sometimes referred to herein as stabilized polymer, will retain small quantities of the amide group-containing solvent, e.g., typically 5.0 weight percent or less, preferably about 1.0 weight percent or less, sometimes about 0.05 weight percent or less. Also, PEA treated in accordance with the invention will typically retain only small quantities of liquid medium, e.g., typically about 1.0 weight percent or less, sometimes 0.05 weight percent or less.

The ratio of liquid medium and amide group-containing solvent is typically preferably about 1:1. It will be understood that other ratios of liquid medium and solvent may be used in accordance with the present invention. Amide group-containing solvents are typically very good solvents for PEA but may contain trace amounts of moisture. Because the moisture may lead to degradation of the polymer, thereby tending to limit the in vivo performance of a device incorporating the polymer, it is typically desirable to minimize how much of the solvent is used, using only enough to fully dissolve the PEA. Minimizing the amount of solvent used, e.g., by first suspending the PEA in a liquid medium, also facilitates precipitation of the polymer from the solvent and removal of the solvent as well.

The solution is heated, typically while stirring, to the boiling point of the liquid medium, to facilitate dissolving the PEA. It has been observed that while the PEA is dissolving in the amide group-containing solvent some bubbling or foaming may be observed. This action ceases once the PEA is fully dissolved. Also, the liquid mixture tends to turn clear once the PEA is fully dissolved. After the PEA is fully dissolved, it is precipitated from solution. Illustrative means of causing the PEA to precipitate include one or more of 1) allowing the solution to cool slowly, 2) adding additional amounts of liquid medium, preferably at the same temperature as the solution, and/or 3) pouring the solution into liquid medium (perhaps a different liquid than was used for suspension). To avoid agglomeration of polymer and obtain uniform treatment, stirring speed may be increased. Small amounts of hot liquid medium may be added to control or temper the rate of cooling and rate of precipitation (by reducing the solubility of the PEA in the amide group-containing solvent fraction) to help prevent coagulation of polymer. It has been observed that a smoother transition of dissolved PEA to a uniform dispersion of precipitated PEA is most readily achieved when the solution is cooled in such a manner (e.g., via controlled cooling rate, continuous mixing, addition of hot liquid medium, etc.) that a substantially uniform temperature gradient is maintained throughout. Preferred results have been obtained when precipitation was performed in a controlled manner such that the resultant precipitated PEA was in a smooth slush-like dispersion. When cooling for precipitation was performed too rapidly, a solid, wax-like build up of material on the walls of the vessel was observed.

In instances where the polymer has merely been extracted or washed with the amide group-containing solvent, separation can typically be achieved by filtration. As used herein, "extraction" refers to the process of contacting, possibly while heating and/or mixing the mixture, the PEA with an amide group-containing solvent but substantially not dissolving the PEA in the solvent. An advantage of treating the PEA in this manner is that separation of the polymer from the solvent is easier and does not require precipitation. Treating by dissolving in the solvent typically provides better stabilization results as compared to mere extraction, however.

Substantially all of the synthesis residues, e.g., acid chloride functionalities, remain dissolved in the solvent. The PEA, still suspended in the liquid medium can be separated, e.g., by filtering, permitting removal of the solvent. It can then be dried, e.g., by tumbling under a vacuum, thereby removing the liquid medium and remaining portions of solvent, leaving the stabilized PEA in powder form. As mentioned above, PEA polymers treated in accordance with the invention may contain trace amounts of the amide group-containing solvent and liquid medium. An advantage of the invention is that toxicologically acceptable liquid mediums and amide group-containing solvents may be used.

In order to evaluate thermal stability, PEA polymers were melted using an Instron Model 4202 Melt Rheometer. A 10 gram sample was used each time and each sample was held for 10 minutes in the rheometer. Inherent viscosity was determined after each melting and the data were recorded. Melt samples at elevated temperatures of poly(esteramides) with and without treatment in accordance with the invention were analyzed for molecular weight distribution using gel permeation chromatography (GPC). It has been found from such data that the treatment of poly(esteramides) in accordance with the invention results in a significant improvement in retention of molecular weight after melt processing in the temperature range of greatest utility (i.e., 170° to 180° C.).

The polymeric materials of this invention can be fabricated into films and fibers by melt extrusion. When the polymer is fabricated into fibers, it is preferred that n of the general formula have an average value from about 50 to about 200. Such fibers have been implanted subcutaneously in rats and have been found to be non-irritating and compatible with the living tissue over the time span of many months.

The polymers of the present invention are also useful in the manufacture of cast and/or extruded films and molded solid surgical aids. Thus, cylindrical pins, screws, reinforcing plates, etc. may be machined from the cast or molded polymer having the aforementioned in vivo absorption characteristics.

In many applications, it is preferred that the polymer have a relatively high molecular weight, i.e., corresponding to an inherent viscosity of about 1.3 to about 1.5. One particularly useful class of poly(esteramide) polymers are those made with ethylenediamine, i.e., $R^3$ is an ethylene group. Such polymers have been found to provide good strength retention properties while providing relatively rapid absorption. However, such polymers have also been observed to be subject to substantial molecular weight degradation during storage and under melt processing conditions except when treated in accordance with the invention. In that instance, they have exhibited marked improvement in storage and heat stability.

EXAMPLES

The invention will be further explained by the following illustrative examples which are intended to be nonlimiting.

EXAMPLE 1

Synthesis and Treatment of Poly[decane-1,10-di(carbonyloxy)ethane-1,2-di(amidocarbonylmethylene)]

Exactly 500 grams ("g") of 1,2-di(hydroxyacetamido)ethane was mixed well with 1.5 liters ("l") of dry toluene and placed in a 22 l flask. To this mixture was added 3.5 l of toluene and then 758.29 g of distilled dodecanedioyl chloride. The mixture was heated and stirred under nitrogen at 90° C. for six hours, then at reflux for about three hours. About 1.5 l of hot toluene was added. The inherent viscosity of the resultant PEA polymer was measured periodically until it reached 1.2, then exactly two liters of dry N-methylpyrrolidone was added. The mixture was heated to and held at 115° C. until the polymer dissolved (20 to 30 minutes). The solution was then allowed to cool to 90° C. and 4 l of hot toluene were added in portions when the solution appeared to change from lustrous to grainy as precipitation of polymer began. The slurry was then heated at 100° C. and mixed for 15 minutes before filtration. The polymer was separated by filtration under nitrogen, then dried in a vacuum oven tumble drier for about three hours to remove solvent, then dried in the dryer over 16 hours at 90° to 100° C. to remove N-methylpyrrolidone.

The product having an inherent viscosity of about 1.1, was stored in a dry box. The thermal stability of this polymer was evaluated by melting the polymer in a rheometer at different temperatures and holding it at the temperature for a period. The following results were obtained:

TABLE I

| Temperature | Inherent Viscosity[1] | | |
|---|---|---|---|
| (°C.) | 10 | 20 | 30 |
| 165 | 1.05 | 1.02 | 1.02 |
| 170 | 0.97 | 0.93 | 0.91 |
| 175 | 0.93 | 0.87 | 0.83 |
| 180 | 0.84 | 0.77 | 0.61 |
| 185 | 0.78 | 0.66 | — |
| 190 | 0.73 | — | — |

[1] In deciliters/gram after the indicated number of minutes had elapsed.

This indicates that the polymer was relatively stable at temperatures up to about 175° C. The polymer exhibits improved stability at all temperatures relative to the same polymer which had not been treated in accordance with the invention.

EXAMPLE 2

Synthesis and Treatment of Poly[decane-1,10-di(carbonyloxy)ethane-1,2-di(amidocarbonylmethyl-methylene)]

Exactly 30 g of 1,2-di(alpha-hydroxypropionamido)ethane prepared from L-lactic acid and ethylenediamine was mixed well with 0.35 l of dry toluene and placed in a large flask. To this mixture was added 39 g of distilled dodecanedioyl chloride. The mixture was heated and stirred under nitrogen at 90° C. for about one hour, then at reflux for about one hour. The inherent viscosity of the polymer samples was measured until it reached 1.2, then the reaction mixture thickened to a solid and 0.030 liters of dry N-methylpyrrolidone was added. The mixture was heated to 115° C. while hydrogen chloride evolved and more N-methylpyrrolidone (0.020 liter was added) until the polymer dissolved (20 to 30 minutes). The solution was then poured into 3 l of ethyl acetate with mixing to cause precipitation of the polymer. The snow-white polymer was separated by filtration under nitrogen, then dried in a vacuum oven for 16 hours at 90° to 100° C. to remove ethyl acetate and N-methylpyrrolidone.

The product having an inherent viscosity of about 1.5 was stored in a dry box. Fibers made from the polymer of this Example were found to be more resistant to hydrolysis than were fibers made from the polymer of Example 1.

EXAMPLE 3

Synthesis and Treatment of Poly[hexane-1,6-di(carbonyloxy)ethane-1,2-di(amidocarbonylmethylene)]

Exactly 10 g of 1,2-di(hydroxyacetamido)ethane was mixed well with 0.15 l of dry toluene in a 0.25 l flask. About 0.050 l of toluene was distilled off while heating the mixture to remove moisture and disperse the diamide diol. To this mixture at about 60° C. was added 11.98 g of distilled suberoyl chloride. The mixture was heated and stirred under nitrogen at 60° C. for one hour, then at 70° C. for one hour, then at 80° C. for one hour and finally at reflux for 0.5 hour. The inherent viscosity of a polymer sample was measured after drying as 0.95, then exactly 0.2 l of dry N-methylpyrrolidone was added. The mixture was heated to and held at 115° C. until the polymer dissolved (20 to 30 minutes). The solution was then allowed to cool to 90° C. and 0.4 l of hot toluene were added in portions when the solution appeared to change from lustrous to grainy as precipitation of polymer began. The slurry was then heated at 100° C. and mixed for 15 minutes before filtration. The polymer was separated by filtration while hot, then dried under vacuum at 80° C.

The product having an inherent viscosity of about 0.95 was stored in a dry box.

EXAMPLE 4

Synthesis and Treatment of Poly[tetradecane-1,14-di(carbonyloxy)ethane-1,2-di(amidocarbonylmethylene)]

Exactly 4.89 g of 1,2-di(hydroxyacetamido) ethane was mixed well with 0.05 l of dry toluene and placed in a large flask. To this mixture was added 8.975 g of distilled hexadecanedioyl chloride. The mixture was heated and stirred under nitrogen at 70° C. for two hours and then at 90° C. for about two hours, then at reflux for about 0.75 hour. To this reaction mixture was added 0.080 l of dry N-methylpyrrolidone. The polymer dissolved (20 to 30 minutes). To the solution was then added hot toluene with mixing to cause precipitation of the polymer. The white polymer was separated by filtration under nitrogen, then dried in a vacuum oven for 16 hours at 80° C. to remove toluene and N-methylpyrrolidone.

The product was not soluble in 2,2,2-trifluoroethanol due to its increased hydrocarbon content therefore its inherent viscosity could not be determined by that method. Based on its smooth, uniform appearance and the lack of lumps, it is believed that the polymer did not gel during synthesis. Filaments pulled from a melted sample of polymer were easily cold drawn by hand to give tenacious fiber indicating that a satisfactory inherent viscosity (and therefore molecular weight) had been obtained.

EXAMPLE 5

Synthesis and Treatment of Poly[oxysuccinoyloxydodecane-1,12-di(amidocarbonylmethylene)]

Exactly 40 g of 1,12-di(hydroxyacetamido)dodecane was mixed well with 0.5 l of dry toluene and placed in a large flask and heated to obtain a solution. To this solution was added slowly 19.6 g of distilled succinoyl chloride. The mixture was heated and stirred under nitrogen at 70° C. for three hours, then at reflux for about two hours. The toluene was removed by filtration. The polymer was dried in vacuum at 80° C. overnight. A portion (24 g) of the solid polymer was placed in a flask and heated on an oil bath at 120° C. under nitrogen with overhead stirring, then 100 milliliters ("ml") of dry N-methylpyrrolidone and an equal volume of dry toluene was added. The mixture was maintained at 120° C. until the polymer dissolved (about 10 minutes). Hot toluene (100 ml) was added. The solution was allowed to cool to 85° C. and 150 ml of hot toluene was added slowly when the solution appeared to thicken. The slurry was then heated at 120° C. and mixed for 15 minutes before filtration. The polymer was separated by filtration under nitrogen, then dried in a vacuum oven tumble drier for about 16 hours at 80° C. to remove solvent. The product having an inherent viscosity of about 1.16, was stored in a dry box.

Using a sample of the polymer which had not been treated with N-methyprrolidone (NMP) and a sample of the same polymer which had been synthesized in the same way but not treated with NMP, a comparison of the inherent viscosities was made at various temperatures as follows:

TABLE II

| Temperature | Inherent Viscosity (dl/g) | |
| --- | --- | --- |
| (°C.) | NMP Treated | Untreated |
| 150 | 1.16 | 1.05 |
| 170 | 1.04 | 0.80 |
| 180 | 1.04 | 0.71 |
| 190 | 0.82 | 0.69 |
| 200 | 0.78 | 0.65 |
| 210 | 0.72 | 0.53 |
| 220 | 0.64 | 0.50 |

These results indicate that treated polymer could be successfully extruded at 180° C. with no substantial deterioration.

EXAMPLE 6

Synthesis and Treatment of Poly[oxysuccinoyloxyhexane-1,6-di(amidocarbonylmethylene)]

A dispersion of 40 g of 1,6-di(hydroxyacetamido)hexane in 100 ml of toluene was added to 250 ml of toluene dried by distilling off 100 ml of an initial portion of 350 ml. The mixture was allowed to cool to about 60° C. and 26.7 g of succinoyl chloride was added. The temperature of the mixture was maintained at 65° C. for 2.5 hours, then raised to 90° C. for two hours. The mixture was then heated at reflux for about 1.5 hours. The inherent viscosity of samples of the reaction mixture was measured at the end of each temperature run and was observed to increase gradually. After the completion of reflux the mixture was filtered hot to isolate the solid polymer and the polymer was dried in vacuo at 100° C. overnight. The inherent viscosity was measured to be 1.1. A 24 g portion of the polymer was mixed under a nitrogen atmosphere with 100 ml of toluene and 60 ml of N-methylpyrrolidone. The mixture was heated to 110° C. and maintained at that temperature until the polymer dissolved (about 0.5 hour). The mixture was then allowed to cool until it began to solidify. Hot toluene was added to the mixture and the polymer solidified. The solid polymer was separated from the hot liquid by filtration and dried in vacuo overnight at 100° C.

The inherent viscosity was measured after drying to be 1.1.

The effect upon heat stability achieved by the present invention in Examples 1, 3, 5, and 6 was evaluated by measuring the inherent viscosity dl/g of the polymer produced in each example before and after heating to 170° C. for 10 minutes. The same measurements were taken of polymers of the same composition but not treated with an amide group-containing solvent in accordance with the invention.

TABLE III

| | Without Treatment | | With Treatment | |
| --- | --- | --- | --- | --- |
| Example | Initial | Final | Initial | Final |
| 1 | 1.2 | 0.31 | 1.2 | 1.18 |
| 3 | 1.1 | 0.67 | 1.2 | 1.18 |
| 5 | 1.05 | 0.8 | 1.16 | 1.04 |
| 6 | 1.1 | 0.55 | 1.1 | 0.64 |

EXAMPLE 7

Synthesis and Treatment of Poly[decane-1,10-di(carbonyloxy)ethane-1,2-di(amidocarbonylmethylene)]

Exactly 500 g of 1,2-di(hydroxyacetoamido)ethane was mixed well with 1.5 l of dry toluene and placed in a 22 l flask. To this mixture was added 3.5 l of toluene and then 758.29 g of distilled dodecanedioyl chloride. The mixture was heated and stirred under nitrogen at 90° C. for 6 hours, then at reflux until the inherent viscosity of the polymer was greater than 1.2. About 1.5 l of hot toluene was then added and the mixture heated at reflux for 2 hours. The inherent viscosity of the polymer was measured periodically until it reached 1.2 when 1.3 l of dry N-methylpyrrolidone and 1.3 l of dry N,N-dimethylformamide were added. The mixture was heated to and held at 115° C. until the polymer had completely dissolved (taking about 20 to 30 minutes). The solution was allowed to cool to 90° C. and 4 l of hot toluene were added in portions when the solution appeared to change from lustrous to grainy appearance as precipitation of polymer began. The slurry was then heated at 100° C. and mixed for 15 minutes before filtration under nitrogen, then dried in a vacuum oven tumble drier for about 3 hours to remove solvent, then dried for 16 hours at 90° to 100° C. to remove the amide group-containing solvents.

The resultant product, a white powder, had an inherent viscosity of about 1.16 and was stored in a dry box. After melting to 170° C., the product had an inherent viscosity of 1.12 and appeared to be whiter than the polymer of Example 1 after melting.

EXAMPLE 8

To a mixture of 20 g of 1,2-di(hydroxyacetamido)ethane in 200 ml of dry toluene was added 7.58 g of dodecanedioyl chloride, 5.995 g of suberoyl chloride, 6.79 g of sebacoyl chloride, and 5.198 g of adipoyl chloride. The mixture was heated to 80° C. and held at that temperature for 6 hours. The mixture was then heated to boiling and polymer began to precipitate. To this hot mixture was added 100 ml of N-methylpyrrolidone in which the polymer dissolved. The mixture was heated to reflux for 2 hours. The polymer was then precipitated by the addition of hot toluene. After being allowed to precipitate, the polymer was separated from the composition by filtration. It was then dried in a vacuum oven at 100° C.

The inherent viscosity was determined to be 0.85.

EXAMPLE 9

A mixture of about 300 ml of dry toluene and 9.9 g of 1,2-di(hydroxyacetoamido)ethane suspended in about 100 ml of toluene was distilled to remove about 100 ml of toluene. The mixture was cooled to and held at 90° C. while adding 30.0 g of dodecanedioyl chloride. The mixture was heated at 90° C. for 2 hours then 11.39 g of 1,2-di(alpha-hydroxypropionamido)ethane was added. The mixture was heated for an additional 2 hours at 90° C., then heated to 100° C. After one hour at 100° C. the inherent viscosity was 1.19. To this mixture was added 100 ml of N-methylpyrrolidone. The solution was then held at 100° C. for 1.5 hours. The mixture was then cooled to 80° C., then reheated to and held at 100° C. for 0.5 hour. The polymer was precipitated by addition of ethyl acetate, separated by filtration, and dried under vacuum at 100° C.

The inherent viscosity was determined to be 1.25.

Various modifications and alterations of this invention will become apparent to those skilled in the art without departing from the scope and spirit of this invention.

What is claimed is:

1. A process for treating poly(esteramide) polymer to increase the stability thereof, said process comprising:
   a) providing a polymer having the following formula:

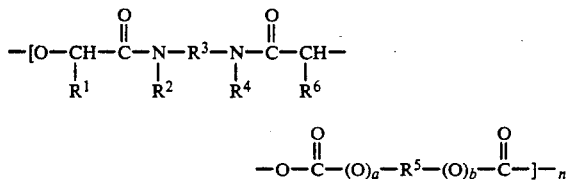

wherein
   1) $R^1$ and $R^6$ are identical or different and are hydrogen or methyl;
   2) $R^3$ and $R^5$ are identical or different and are selected from the group consisting of the following, which are linear or branched, alkylene, alkylene having 1 or 2 nonadjacent catenary oxygen or sulfur atoms, alkenylene, cycloalkylene and arylene; said members of the group having up to 25 carbon atoms in the cyclic compounds and from 2 to 25 carbon atoms in the non-cyclic compounds;
   3) $R^2$ and $R^4$ are identical or different and are hydrogen or alkyl having 1 to 4 carbon atoms or $R^2$ and $R^4$ together are linear or branched alkylene having one to four carbons forming with N—$R^3$—N a heterocyclic group having 5 or 6 ring atoms;
   4) a and b are independently zero or one; and
   5) n having an average value from about 10 to about 400;
   b) treating said polymer with an amide group-containing solvent; and
   c) separating said polymer from said amide group-containing solvent to yield stabilized polymer.

2. The process of claim 1 wherein said amide group-containing solvent is selected from at least one of the following: N-methylpyrrolidone, N-methylformamide, N-methylacetamide, formamide, N,N-dimethylformamide, N,N-dimethylacetamide, and tetramethylurea.

3. The process of claim 1 wherein said amide group-containing solvent is N-methylpyrrolidone.

4. The process of claim 1 further comprising suspending said polymer in a non-reactive liquid medium.

5. The process of claim 4 wherein said liquid medium is an aprotic liquid.

6. The process of claim 4 wherein said liquid medium is one or more of the following: methyl chloroacetate, toluene, chlorobenzene, xylene, 1,1,2-trichloroethane, or 1,4-dioxane.

7. The process of claim 4 wherein said liquid medium is toluene.

8. The process of claim 4 further comprising substantially removing said liquid medium and amide group-containing solvent from said stabilized polymer.

9. The process of claim 4 wherein said liquid medium is a solvent for but is non-reactive with diacid chloride.

10. The process of claim 4 wherein said liquid medium is a non-solvent for diamidediol.

11. The process of claim 4 wherein said liquid medium is anhydrous.

12. The process of claim 4 wherein said liquid medium has a boiling point between about 70° and about 150° C.

13. The process of claim 4 wherein said liquid medium has a boiling point between about 90° and about 120° C.

14. The process of claim 4 wherein said stabilized polymer contains about 1.0 weight percent or less of said liquid medium.

15. The process of claim 4 wherein said stabilized polymer contains about 0.05 weight percent or less of said liquid medium.

16. The process of claim 1 wherein said stabilized polymer is yielded in dry form.

17. The process of claim 1 wherein $R^3$ is a two carbon alkylene.

18. The process of claim 1 wherein said treating comprises extracting said polymer with said amide group-containing solvent and said separating comprises filtering said stabilized polymer.

19. The process of claim 1 wherein said treating comprises dissolving said polymer in said amide group-containing solvent and said separating comprises precipitating said stabilized polymer.

20. The process of claim 19 wherein said stabilized polymer is precipitated by cooling the solution.

21. The process of claim 20 wherein said solution is cooled so as to maintain a substantially uniform temperature gradient throughout the solution.

22. The process of claim 1 further comprising vacuum drying.

23. The process of claim 1 wherein said stabilized polymer contains about 5.0 weight percent or less of said amide group-containing solvent.

24. The process of claim 1 wherein said stabilized polymer contains about 1.0 weight percent or less of said amide group-containing solvent.

25. The process of claim 1 wherein said stabilized polymer contains about 0.05 weight percent or less of said amide group-containing solvent.

26. The process of claim 1 wherein said polymer is made by:
   a) reacting a diamine with one or more of lactic or glycolic acid to form a diamidediol; and then
   b) reacting said diamidediol with a compound selected from the group consisting of: dicarboxylic acids, methyl and ethyl esters of dicarboxylic acids, diacid chlorides and anhydrides of a dicarboxylic acid;
to form said poly(esteramide) polymer.

27. The process of claim 26 wherein in said step b), said diamidediol is suspended in a liquid medium when reacted with said compound, said liquid medium being a non-solvent for and non-reactive with said diamidediol and said compound, and being a non-reactive solvent for said compound.

28. The process of claim 27 wherein said liquid medium is toluene.

29. The process of claim 26 wherein said poly(esteramide) is synthesized and dissolved in an amide group-containing solvent in the same vessel.

30. A poly(esteramide) treated in accordance with claim 1.

31. A poly(esteramide) polymer having the following formula:

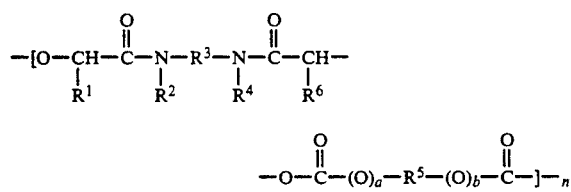

wherein
1) $R^1$ and $R^6$ are identical or different and are hydrogen or methyl;
2) $R^3$ and $R^5$ are identical or different and are selected from the group consisting of the following, which are linear or branched, alkylene, alkylene having 1 or 2 nonadjacent catenary oxygen or sulfur atoms, alkenylene, cycloalkylene and arylene; said members of the group having up to 25 carbon atoms in the cyclic compounds and from 2 to 25 carbon atoms in the non-cyclic compounds;
3) $R^2$ and $R^4$ are identical or different and are hydrogen or alkyl having 1 to 4 carbon atoms or $R^2$ and $R^4$ together are linear or branched alkylene having one to four carbons forming with N—$R^3$—N a heterocyclic group having 5 or 6 ring atoms;
4) a and b are independently zero or one; and
4) n having an average value from about 10 to about 400;
said polymer containing trace amounts of an amide group-containing solvent.

32. The polymer of claim 31 wherein said polymer contains about 5.0 weight percent or less of an amide group-containing solvent.

33. The polymer of claim 31 wherein said polymer contains about 1.0 weight percent or less of said amide group-containing solvent.

34. The polymer of claim 31 wherein said polymer contains about 0.05 weight percent or less of said amide group-containing solvent.

35. The polymer of claim 31 wherein said polymer contains about 1.0 weight percent or less of said liquid medium.

36. The polymer of claim 31 wherein said polymer contains about 0.05 weight percent or less of said liquid medium.

37. The polymer of claim 11 wherein $R^3$ is a two carbon alkylene.

38. A device for in vivo implantation which comprises a polymer of claim 31.

39. An article comprising the polymer of claim 31.

* * * * *

UNITED STATES PATENT AND TRADEMARK OFFICE
CERTIFICATE OF CORRECTION

PATENT NO. : 5,286,837
DATED : February 15, 1994
INVENTOR(S) : Thomas H. Barrows et al.

It is certified that error appears in the above-identified patent and that said Letters Patent is hereby corrected as shown below:

In Column 6, Line 34, insert the word --preferred-- between the words "the" and "process".

In Column 6, Line 35, delete the word "preferred".

Signed and Sealed this

Twenty-seventh Day of September, 1994

*Attest:*

BRUCE LEHMAN

*Attesting Officer*     *Commissioner of Patents and Trademarks*